(12) United States Patent
Raghunath et al.

(10) Patent No.: US 9,446,031 B2
(45) Date of Patent: Sep. 20, 2016

(54) COMPOSITIONS AND METHODS FOR NEOVASCULARIZATION

(71) Applicants: National University of Singapore, Singapore (SG); Massachusetts Institute of Technology, Cambridge, MA (US)

(72) Inventors: Michael Raghunath, Singapore (SG); Sei Hien Lim, Singapore (SG); Roger Dale Kamm, Cambridge, MA (US)

(73) Assignees: National University of Singapore, Singapore (SG); Massachusetts Institute of Technology, Cambridge, MA (US)

(*) Notice: Subject to any disclaimer, the term of this patent is extended or adjusted under 35 U.S.C. 154(b) by 146 days.

(21) Appl. No.: 13/743,223

(22) Filed: Jan. 16, 2013

(65) Prior Publication Data

US 2013/0197038 A1 Aug. 1, 2013

Related U.S. Application Data

(60) Provisional application No. 61/587,713, filed on Jan. 18, 2012.

(51) Int. Cl.

| | | |
|---|---|---|
| *A01N 43/40* | (2006.01) | |
| *A61K 31/44* | (2006.01) | |
| *A01N 43/00* | (2006.01) | |
| *A61K 31/397* | (2006.01) | |
| *A61K 31/4412* | (2006.01) | |
| *C12N 5/07* | (2010.01) | |
| *A61K 31/688* | (2006.01) | |
| *C12N 5/071* | (2010.01) | |

(52) U.S. Cl.
CPC ......... *A61K 31/4412* (2013.01); *A61K 31/688* (2013.01); *C12N 5/06* (2013.01); *C12N 5/069* (2013.01); *C12N 2501/998* (2013.01)

(58) Field of Classification Search
CPC ... A61K 31/4412; A61K 31/688; C12N 5/06
USPC ....................................................... 514/350
See application file for complete search history.

(56) References Cited

U.S. PATENT DOCUMENTS

| | | | |
|---|---|---|---|
| 5,882,914 A | 3/1999 | Semenza | |
| 6,124,131 A | 9/2000 | Semenza | |
| 6,562,799 B1 | 5/2003 | Semenza | |
| 6,660,737 B2 | 12/2003 | Almstead et al. | |
| 6,753,321 B2 | 6/2004 | Kovesdi | |
| 6,838,430 B2 | 1/2005 | Arbeit | |
| 6,986,881 B1 | 1/2006 | Livingston et al. | |
| 7,053,046 B2 | 5/2006 | McGrath | |
| 7,860,545 B2 | 12/2010 | Shults et al. | |
| 8,060,174 B2 | 11/2011 | Simpson et al. | |
| 2002/0115165 A1 | 8/2002 | Stein et al. | |
| 2003/0022838 A1 | 1/2003 | Sheppard et al. | |
| 2003/0176317 A1 | 9/2003 | Guenzler-Pukall et al. | |
| 2005/0227948 A1 | 10/2005 | Schofield et al. | |
| 2006/0023763 A1 | 2/2006 | Farmer et al. | |
| 2006/0141000 A1 | 6/2006 | Mikos et al. | |
| 2006/0198864 A1 | 9/2006 | Shults et al. | |
| 2006/0199836 A1 | 9/2006 | Turtle et al. | |
| 2007/0003589 A1 | 1/2007 | Astafieva et al. | |
| 2009/0110711 A1 | 4/2009 | Trollsas et al. | |
| 2009/0136553 A1 | 5/2009 | Gerlach et al. | |
| 2009/0214616 A1 | 8/2009 | Elbert et al. | |
| 2009/0324681 A1 | 12/2009 | Badylak | |
| 2010/0034794 A1 | 2/2010 | Van der Strate et al. | |
| 2011/0238000 A1 | 9/2011 | Seliktar et al. | |

FOREIGN PATENT DOCUMENTS

| | | |
|---|---|---|
| EP | 1 658 074 B1 | 11/2012 |
| WO | WO 02/15955 A2 | 2/2002 |
| WO | WO 02/074981 A2 | 9/2002 |
| WO | WO 2009/085272 A9 | 7/2009 |
| WO | WO 2010/118298 A2 | 10/2010 |

OTHER PUBLICATIONS

Sefcik et al. ("Engineering vascularized tissues using natural and synthetic small molecules." Organogenesis 4.4 (2008): 215-227).*
Ader et al. ("Sphingosine kinase 1: a new modulator of hypoxia inducible factor 1a during hypoxia in human cancer cells." Cancer research 68.20 (2008): 8635-8642).*
Barron, K., et al., "Comparative Evaluation of the In Vitro Effects of Hydralazine and Hydralazine Acetonide on Arterial Smooth Muscle", *Br. J. Pharmac*, 61:345-349 (1977).
Bhang, S.H., et al., "Combined Gene Therapy With Hypoxia-Inducible Facotr-1α and Heme Oxygenase-1 for Therapeutic Angiogenesis", *Tissue Engineering: Part A*, 17(7-8):915-926 (2011).
Blumenkrantz, N., et al., "Effect of Hydralazine and Dihydralazine on Connective Tissue and Binding to Serum Protein", *Scandinavian Journal of Rheumatology*, 8(3): 177-183 (1979).
Bracken, C.P., et al., "The Hypoxia-Inducible Factors: Key Transcriptional Regulators of Hypoxic Responses", *Cell Mol. Life Sci*, 60(7): 1376-1393 (2003).
Brey. E. M., et al., "Therapeutic Neovascularization: Contributions From Bioengineering", *Tissue Eng*, 11(3-4): 567-584 (2005).
Bruick, R.K., "Transcription Oxygen Sensing Gets a Second Wind", *Science*, 295(5556): 807-808 (2002).
Chen, X., et al., "Prevascularization of a Fibrin-Based Tissue Construct Accelerates the Formation of Functional Anastomosis With Host Vasculature", *Tissue Engineering: Part A*, 15(6):1363-1371 (2009).

(Continued)

*Primary Examiner* — Layla Soroush
(74) *Attorney, Agent, or Firm* — Hamilton, Brook, Smith & Reynolds, P.C.

(57) ABSTRACT

The invention is directed to a method of inducing angiogenesis at a site in an individual in need thereof comprising administering locally to the site an effective amount of one or more agents that induce hypoxia induced factor 1α (HIF-1α). In another aspect, the invention is directed to a method of inducing angiogenesis at a site in an individual in need thereof comprising administering locally to the site an effective amount of one or more agents that induce hypoxia induced factor 1α (HIF-1α) and one or more lysophospholipids. In addition, the invention is directed to methods of generating prevascularized tissue, methods of generating a vascular network in a device and compositions thereof.

4 Claims, 5 Drawing Sheets

(56) References Cited

OTHER PUBLICATIONS

Chiu, Y.C., et al., "Materials for Engineering Vascularized Adipose Tissue", *Journal of Tissue Viability*, 20:37-48 (2011).

Clement, P.M.J., et al., "The Antifungal Drug Ciclopirox Inhibits Deoxyhypusine and Proline Hydroxylation, Endothelial Cell Growth and Angiogenesis In Vitro", *Int. J. Cancer*, 100: 491-498 (2002).

English, D., "Sphingosine 1-Phosphate Released From Platelets Druing Clotting Accounts for the Potent Endothelial Cell Chemotactic Activity of Blood Scrum and Provides a Novel Link Between Hemostatis and Angiogenesis", *FASEB J*, 14: 2255-2265 (2000).

Gleadle, J. M., et al., "Regulation of Angiogenic Growth Factor Expression by Hypoxia, Transition Metals, and Chelating Agents", *Am J Physiol*, 268: C1362-C1368 (1995).

Griffith, C.K. and George, S.C., "The Effect of Hypoxia on In Vitro Prevascularization of a Thick Soft Tissue", *Tissue Engineering: Part A*, 15(9):24232434 (2009).

Hokugo, A., et al., "Preparation of Prefabricated Vascularized Bone Graft With Neoangiogenesis by Combination of Autologous Tissue and Biodegradable Materials", *International Journal of Oral and Maxillofacial Surgery*, 35(11):1034-1040 (2006).

Huang, Y.T., et al., "Sphingosine 1-Phosphate Induces Platelet/Endothelial Cell Adhesion Molecule-1 Phosphorylation in Human Endothelial Cells Through cSrc and Fyn", *Cell Signal*, 20(8): 1521-1527 (2008).

Israili, Z.H. and Dayton, P.G., "Metabolism of Hydralazine", *Drug Metabolism Reviews*, 6(2): 283-305 (1977).

Jeziorska, M. and Woolley, D.E., "Local Neovascularization and Cellular Composition Within Vulnerable Regions of Atherosclerotic Plaques of Human Carotid Arteries", *Journal of Pathology*, 188(2):189-196 (1999).

Kaelin, Jr., William G., "Proline Hydroxylation and Gene Expression", *Annu Rev. Biochem*, 74: 115-128 (2005).

Kannan, R.Y., et al., "The Roles of Tissue Engineering and Vascularization in the Development of Micro-Vascular Networks: A Review", *Biomaterials*, 26(14):1857-1875 (2005).

Kim, C., et al., "Rapid Exchange of Oil-Phase in Microencapsulation Chip to Enhance Cell Viability", *Lab Chip*, 9(9):1294-1297 (2009).

Knowles, H.J., et al., "Novel Mechanism of Action for Hydralazine Induction of Hypoxia-Inducible Factor-1α, Vascular Endothelial Growth Factor, and Angiogenesis by Inhibition of Prolyl Hydroxylases", *Cir. Res.*, 95: 162-169 (2004).

Koike, N., et al., "Tissue Engineering: Creation of Long-Lasting Blood Vessels", *Nature*, 428(6979): 138-139 (2004).

Lee, O.H., et al., "Sphingosine 1-Phosphate Induces Angiogenesis: Its Angiogenic Action and Signaling Mechanism in Human Umbilical Vein Endothelial Cells", *Biochem Biophys Res Comm*, 264(3): 743-750 (1999).

Levceberg, S., et al., "Engineering Vascularized Skeletal Muscle Tissue", *Nature Biotechnology*, 23(7): 879-884 (2005).

Lovett, M., et al., "Vascularization Strategies for Tissue Engineering", *Tissue Engineering: Part B*, 15(3):353-370 (2009).

Luo, Y., et al., "A Constitutively Active Hypoxia-Inducible Factor-1α/VP16 Hybrid Factor Activates Expression of the Human B-Type Natriuretic Peptide Gene", *Molecular Pharmacology*, 69(6): 1953-1962 (2006).

McKenzie, D.L., et al., "A Potent New Class of Reductively Activated Peptide Gene Delivery Agents", *Journal of Biololgical Chemistry*, 275(14): 9970-9977 (2000).

Melnikova, I., "Aneamia Therapies", *Nature Review Drug Discovery*, 5: 627-628 (2006).

Mertsching, H., et al., "Engineering of a Vascularized Scaffold for Artificial Tissue and Organ Generation", *Biomaterials*, 26(33): 6610-6617 (2005).

Mikos, A.G., et al., "Prevascularization of Porous Biodegradable Polymers", *Biotechnology and Bioengineering*, 42: 716-723 (1993).

Murad, S., et al., "A Paradoxical Effect of Hydralazine on Prolyl and Lysyl Hydroxylase Activities in Cultured Skin Fibroblasts", *Arch Biochem Biophys*, 241(2): 356-363 (1985).

Nomi, M., et al., "Principals of Neovascularization for Tissue Engineering", *Mol Aspects Med*, 23(6): 463-483 (2002).

Ozawa, C.R., et al., "Microenvironmental VEGF Concentration, Not Total Dose, Determines a Threhold Between Normal and Aberrant Angiogenesis", *The Journal of Clinical Investigation*, 113(4): 516-527 (2004).

Parrill, A.L., "Lysophospholipid Interactions With Protein Targets", *Biochim Biophys Acta.*, 1781(9):540-564 (2008).

Perets, A., et al., "Enhancing the Vascularization of Three-Dimensional Porous Alginate Scaffolds by Incorporating Controlled Release Basic Fibroblast Growth Factor Microspheres", *J. Biomed Mater Res*, 65A:489-497 (2003).

Rafii, S. and Lyden, D., "Therapeutic Stem and Progenitor Cell Transplantation for Organ Vascularization and Regeneration", *Nature Medicine*, 9(6): 702-712 (2003).

Ragunath, M. et al., "Pharmacologically Induced Angiogenesis in Transgenic Zebrafish", *Biochem Biophys Res Commun.*, 378(4):766-771 (2009).

Ratner, B.D., "Reducing Capsular Thickness and Enhancing Angiogenesis Around Implant Drug Release Systems", *Journal of Controlled Release*, 78:211-218 (2002).

Richardson, T.P., et al., "Polymeric System for Dual Growth Factor Delivery", *Nature Biotechnology*, 19:10291034 (2001).

Rivron, N.C., et al., "Engineering Vascularised Tissues In Vitro", *European Cells and Materials*, 15:27-40 (2008).

Rosen, H. and Goetzl, E.J., "Sphingosine 1-Phosphate and Its Receptors: An Autocrine and Paracrine Network", *Nature Review Immunology*, 5(7): 560-570 (2005).

Saif, J., et al., "Combination of Injectable Multiple Growth Factor-Releasing Scaffolds and Cell Therapy As an Advanced Modality to Enhance Tissue Neovascularization", *Arteriorscler Thomb Vasc Biol.*, 30:1897-1904 (2010).

Sasagawa, T., et al., "Design of Prevascularized Three-Dimensional Cell-Dense Tissues Using a Cell Sheet Stacking Mainpulation Technology", *Biomaterials*, 31: 1646-1654 (2010).

Semenza, G.L., "HIF-1: Mediator of Physiological and Pathophysiological Responses to Hypoxia", *J Appl Physiol*, 88:1474-1480 (2000).

Semenza, G.L., "Targeting HIF-1 for Cancer Therapy", *Nature Reviews Cancer*, 3(10): 721-732 (2003).

Soker, S., et al., "Systems for Therapeutic Angiogenesis in Tissue Engineering", *World J Urol*, 18(1): 10-18 (2000).

Sun, G., et al., "Functional Neovascularization of Biodegradable Dextran Hydrogels With Multiple Angiogenic Growth Factors", *Biomaterials*, 32:95-106 (2011).

Thurston, G., "Complementary Actions of VEGF and Angiopoietin-1 on Blood Vessel Growth and Leakage", *J. Anat.*, 200:575-580 (2002).

Trentin, D., et al., "Peptide-Matrix-Mediated Gene Transfer of an Oxygen-Insensitive Hypoxia-Inducible Factor-1α Variant for Local Induction of Angiogenesis", *PNAS*, 103(8): 2506-2511 (2006).

Tschank, G., et al., "Pyridinedicarboxylates, the First Mechhanism-Derived Inhibitors for Prolyl 4-Hydroxylase, Selectively Supress Cellular Hydroxyprolyl Biosynthesis", *Biochem J.*, 248:625-633 (1987).

van Amerongen, M.J., et al., "Neovascularization and Vascular Markers in a Foreign Body Reaction to Subcutaneously Implanted Degradable Biomatcrial in Mice", *Angiogenesis*, 5: 173-180 (2002).

Vickerman, V., et al., "Design, Fabrication and Implementation of a Novel Multi-Parameter Control Microfluidic Platform for Three-Dimensional Cell Culture and Real-Time Imaging", *Lab Chip*, 8(9): 1468-1477 (2008).

Warnecke, C., et al., "Activation of the Hypoxia-Inducible Factor-Pathway and Stimulation of Angiogenesis by Application of Prolyl

(56) References Cited

OTHER PUBLICATIONS

Hydroxylase Inhibitors", *The FASEB Journal*, 17: 1186-1188 (2003).

Zhang, X., et al., "Functional Neovascularization in Tissue Engineering With Porcine Acellular Dermal Matrix and Human Umbilical Vein Endothelial Cells", *Tissue Engineering: Part C, Methods*, 17(4):423-433 (2011).

Hien, L.S., et al., "Induction of Angiogenesis in Microfluidic Devices Using Prolyl Hydroxylase Inhibitors and Phingosine-1 Phospate"; 1 page poster; presented Jan. 18, 2012.

\* cited by examiner

COMPOSITIONS AND METHODS FOR NEOVASCULARIZATION

RELATED APPLICATION(S)

This application claims the benefit of U.S. Provisional Application No. 61/587,713, filed on Jan. 18, 2012. The entire teachings of the above application are incorporated herein by reference.

BACKGROUND OF THE INVENTION

Angiogenesis represents a major challenge in regenerative medicine and tissue engineering.

Thus, a need exists for compositions and methods for inducing angiogenesis.

SUMMARY OF THE INVENTION

The invention relates to the fields which include tissue engineering, advanced wound care and implantology e.g., where the induction of blood vessel growth in, into and/or around a biomaterial with less fibrotic capsule formation is highly desirable. Described herein are compositions and methods for use in induction (e.g., local induction; pharmacological (local) induction) of angiogenesis which involves the use of an (one or more) agent that induces hypoxia-induced factor 1α (HIF-1α), or a combination of an (one or more) agent that induces hypoxia-induced factor 1α (HIF-1α) and a (one or more) lysophospholipid that protect endothelium and maintain vascular integrity. The methods and compositions can further comprise one or more cell types that support and maintain functional blood vessels.

As described herein, using a microfluidic approach to study the angiogenic effects of agents that induce hypoxia induced factor 1α (HIF-1α), it is shown that endothelial cells sprout towards mesenchymal cells, or fibroblasts under the induction of an (one or more) agent that induces HIF-1α. In addition, endothelial-mesenchymal interactions are shown in the microfluidic model where endothelial cells consistently sprout more aggressively towards fibroblasts than culture medium with an agent that induces HIF-1α. Surprisingly, the angiogenic effects were augmented when a (one or more) lysophospholipid was used in combination with an agent that induces HIF-1α as compared to sole induction of an agent that induces HIF-1α or lysophospholipid.

Accordingly, in one aspect, the invention is directed to a method of inducing angiogenesis at a site in an individual in need thereof comprising administering locally to the site an effective amount of one or more agents that induce hypoxia induced factor 1α (HIF-1α). In another aspect, the invention is directed to a method of inducing angiogenesis at a site in an individual in need thereof comprising administering locally to the site an effective amount of one or more agents that induce hypoxia induced factor 1α (HIF-1α) and one or more lysophospholipids.

Another aspect of the invention is a method of generating prevascularized tissue ex vivo. The method comprises culturing (i) one or more agents that induce hypoxia induced factor 1α (HIF-1α), (ii) one or more cell types that produce angiogenic factors and (iii) one or more cell types that induce angiogenesis, thereby producing a culture. The culture is maintained under conditions in which angiogenesis occurs and prevascularized tissue forms, thereby generating prevascularized tissue ex vivo. The invention is directed to prevascularized tissue produced by the methods described herein and pharmaceutical compositions thereof.

Another aspect of the invention is a composition, including pharmaceutical compositions, comprising (i) a biocompatible matrix, (ii) one or more agents that induce hypoxia induced factor 1α (HIF-1α) and (iii) one or more lysophospholipids.

Another aspect of the invention is a method of generating a vascular network in a device comprising culturing (i) one or more agents that induce hypoxia induced factor 1α (HIF-1α), (ii) one or more cell types that produce angiogenic factors and (iii) one or more cell types that induce angiogenesis, thereby producing a culture. The culture is maintained under conditions in which a vascular network forms in the device, thereby generating a vascular network in the device. The invention is also directed a vascular network produced by the method.

Another aspect of the invention is a an angiogenic assay device comprising (i) one or more agents that induce hypoxia induced factor 1α (HIF-1α), (ii) one or more cell types that produce angiogenic factors and (iii) one or more cell types that induce angiogenesis, wherein the one or more cell types that induce angiogenesis form a vascular network in the presence of the one ore more agents that induce HIF-1α and the one or more cell types that produce angiogenic factors in the device.

and VEGF (11x). CPX appears to be the main compound causing the observed upregulation. (E) and (J): representative images of 3 proteomic profiler membranes showing differences in protein secretion between CPX and S1P treated group and non-treated group (culture media control). (K) and (L): ELISA quantitation of PlGF and VEGF corroborating semi-quantitative results shown in A-I. The negative values in the plots denote the cellular uptake of the measured proteins as opposed to secrete them. * p<0.05

Figure 5:
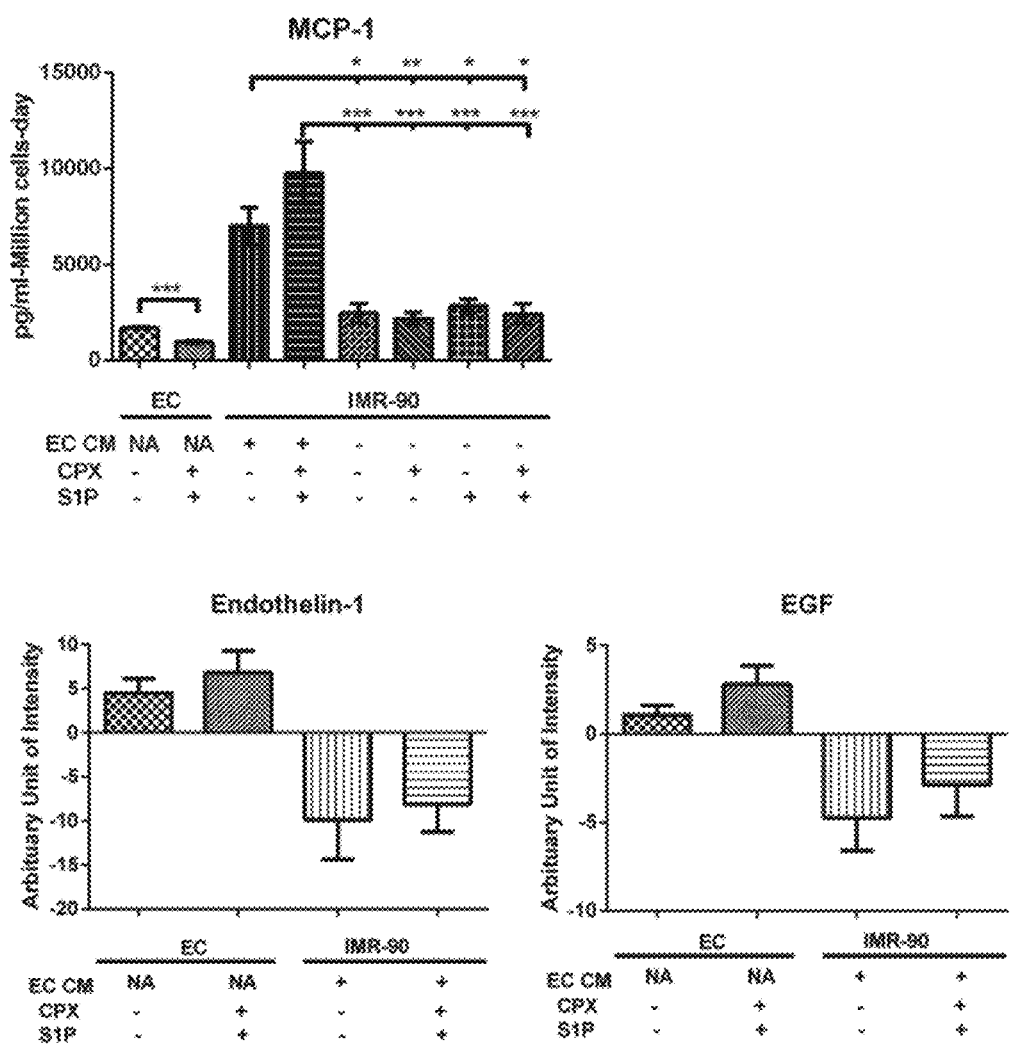

FIG. 5: Endothelial CM modulates growth factor secretion by fibroblasts. (A) ELISA: fibroblasts secrete 5 times more MCP-1 cultured in EC CM. No significant difference in MCP-1 secretion is elicited by CPX or S1P. (B) and (C): semi-quantitative proteomic array plots showing clearance of EC secreted endothelin-1 and EGF from culture media in the presence of fibroblasts. The negative values in the plots suggest either cellular take up or degradation of measured target proteins [* p<0.05].

DETAILED DESCRIPTION OF THE INVENTION

Shown herein is a vascularization strategy in which one or more agents that induces HIF-1α are used to induce angiogenesis (e.g., maximize angiogenic effects). Also shown herein are synergistic effects when one or more agents that induce HIF-1α is used in combination with one or more lysophospholipids to induce angiogenesis. Thus, in one aspect, HIF-1α is used to induce angiogenesis, and in a particular aspect, one or more agents that induce HIF-1α in combination with one or more lysophospholipids is used to induce angiogenesis.

As described herein, these effects were shown using an in vitro microfluidic platform where endothelial cells were co-cultured with fibroblast cells and subjected to the stimulation of one or more agents that induces HIF-1α, and one or more agents that includes HIF-1α in combination with one or more lysophospholipids. The interactions between endothelial cells and mesenchymal cells or fibroblasts maintained immature sprouts and turned them into functional vessels with lumens, and these effects were most prominent when one or more agents that induces HIF-1α were combined with lysophospholipids. Through the measurement of sprout length, it was demonstrated that sprouts had invaded and traveled the longest distance in a collagen I 3D scaffold under the induction of one or more agents that induces HIF-1α and one or more lysophospholipids and the average length was 1.5 fold longer as compared to the sole induction of either an agent that induces HIF-1α or a lysophospholipid. The methods provided herein are useful for angiogenesis (e.g., inducing angiogenesis, such as therapeutic angiogenesis for tissue engineering where neovascularization is required).

Accordingly, in one aspect, the invention is directed to a method of inducing angiogenesis at a site in an individual in need thereof comprising administering locally to the site an effective amount of one or more agents that induce hypoxia induced factor 1α (HIF-1α). In another aspect, the invention is directed to a method of inducing angiogenesis at a site in an individual in need thereof comprising administering locally to the site an effective amount of one or more agents that induce hypoxia induced factor 1α (HIF-1α) and one or more lysophospholipids.

As used herein, angiogenesis (angiopoiesis; vasculogenesis) refers to formation and/or induction of one or more blood vessels (a blood vessel; a vascular network such as a capillary bed) and includes neovascularization and revascularization.

HIF-1α, also referred to herein as HIF-1 and HIF, is a master switch that controls an array of angiogenic genes and subsequent peptide factors, including vascular endothelial growth factor (VEGF) (Semenza, G L, *J Appli Physiol.*, 88(4):1474-1480 (2000); Kaelin, W G, *Ann Rev Biochem*, 74:115-128 (2005)). More than 50 direct target genes of HIF 1 have been identified. In addition, indirect effects of HIF-1α affect hundreds of responsive genes in any given cell including vascular endothelial growth factor (VEGF) and its receptors, the enzymes of glycolysis and inducible nitric oxide synthase (Semenza G L, *Nature Rev Ca*, 3:721-732 (2003), Bracken C P, et al. *Cell Mol Life Sci*, 60:1376-1393 (2003)). HIF-1α has recently gained tremendous interest as target for systemic therapies, e.g., anaemia treatment, since amongst those gene products regulated by HIF is the physiologically important erythropoietin (Melnikova I, *Nat Rev Drug Discov*, 5:627-628 (2006)).

The action of HIF-1 is tightly controlled. Under normal (normoxic) conditions, HIF-1α is quickly degraded because it is constantly hydroxylated at two prolyl residues by prolyl hydroxylase (PH) and at one asparaginyl residue by an asparaginyl hydroxylase (AH). The hydroxylated prolyl sites promote interaction with the von-Hippel Lindau tumor suppressor protein (pVHL). Constant hydroxylation earmarks HIF-1α for proteosomal degradation, therefore, HIF-1 is highly unstable in normoxia (Bruick and McKnight, *Science*, 295(5556): 807-808 (2002)). If oxygen levels drop (hypoxia), both prolyl and asparaginyl residues are not hydroxlated. This has two effects, the degradation of HIF-1 ceases and the transcriptional activator p300 can now bind to HIF-1. As a result, HIF-1 survives and can act as a master switch for the above described HIF-1 dependent genes.

A variety of agents can be used to induce HIF-1α. As used herein, inducing HIF-1α includes enhancing expression and/or activity of HIF-1α. In one aspect, the one or more of agents induce HIF-1α by inhibiting degradation of HIF-1α. Both PH and AH are members of the dioxygenase family. Other human members of this family include deoxyhypusine hydroxylase (Clement et al., *Int J Cancer*, 100:491-498 (2002)) and collagen prolyl hydroxylase (CPH) which catalyses the hydroxylation of specific prolyl residues required to thermostabilise the collagen triple helix. The development of CPH inhibitors to prevent liver cirrhosis was pursued in the late 1980's (Tschank et al., *Biochem J*, 248:625-633 (1987)). The existence of a HIF-PH was unknown at this time point. Since prolyl hydroxylases are oxygen, Fe(II) and 2-oxoglutarate dependent dioxygenases, they are affected not only by hypoxia but also by iron chelation and competitive 2-oxoglutarate analogues.

Prolyl hydroxylase inhibitors (PHis) are compounds that prevent the degradation of hypoxia inducible factor 1α (HIF-1α) in vivo, thus upregulating various angiogenic factors including vascular endothelial growth factor (VEGF) as a response to the induced pseudo-hypoxic condition under normoxia. In addition, PHis reduce fibrosis and prevent fibrotic capsule from forming. With this unique combination of pro-angiogenic and anti-fibrotic properties, PHis are distinct from other single-action approaches.

In a particular aspect, the one or more of the agents that induce HIF-1α comprise a hydroxylase inhibitor, an iron chelator or a combination thereof. The hydroxylase inhibitor can be a prolyl hydroxylase inhibitor (PHi), a collagen prolyl hydroxylase (CPH) inhibitor, an asparaginyl hydroxylase (AH) inhibitor, a deoxyhypusine inhibitor, cobalt ions or a combination thereof. Specific examples of a PHi include ciclopirox olamine (CPX), pyridine dicarboxylic acids, oxalylglycine, cis-proline, L-azetidine, thioenolpuridines, oxoglutarate analogues, or combinations thereof. Specific examples of a CPH inhibitor include hydralazine, biologically derived metabolites of hydralazine (e.g., hydralazine acetonide; hydralazine pyruvate hydrazine (Israili, Z H, et al., Drug Metab Rev, 6(2):283-305 (1977); Barron, K, et al., Br J Pharmacol, 61(3):345-349 (1977)) or combinations thereof. A specific example of an AH inhibitor includes dimethyloxaloylglycine (DMOG); and a specific example of a deoxyhypusine inhibitor includes mimosine. Specific examples of an iron chelator includes desferioxamine, α,α-dipyridine, mimosine, 3,4-dihydroxybenzoate, epolones or combinations thereof.

Lysophospholipids are important mediators of multiple biological events including cell proliferation, survival and angiogenesis through specific cell surface G-protein coupled receptors. They are usually derived from the cells membranes and preferably bind to albumin in extracellular spaces. The lysophospholipids exert their effects through the G protein-coupled receptors (GPCR) and thus triggering downstream signaling.

A variety of lysophospholipids can also be used in the methods and compositions described herein. Specific examples of a lysophospholipid include sphingosine 1-phosphate (SIP), lysophosphatidic acid (LPA), alkyl glycerol phosphate (AGP), cyclic phosphatidic acid (CPA) or combinations thereof.

In the methods and compositions described herein, the one or more agents that induce HIF-1α and the one or more lysophospholipids can be present in a biocompatible matrix (e.g., and administered locally to the site). As will be apparent to those of skill in the art, any of a variety of biocompatible matrices can be used. For example, a biocompatible matrix made of one or more metals, polymeric materials, biopolymers, carbohydrates, inorganic materials or combinations thereof can be used. Examples of a metal that can be used as a biocompatible matrix include titanium, steel, steel alloys, precious metals, copper, amalgams or combinations thereof. Examples of a polymeric materials that can be used as a biocompatible matrix include polyglycolic acid, polystyrene, polybutyrate, polygalactic acid, caprolactonic acid, acrylates, polyacrylate salts, silicones, polyesters, polyamides, polyamines, phthalates, or combinations thereof. Examples of a biopolymers that can be used as a biocompatible matrix include gelatin, collagen and artificial collagen, hyaluronic acid and derivatives, fibrin and modifications, keratin, chitin, chitosan, proteins, fibroins (e.g., derived from spider and silkworm), elastin, bone, coral, or combinations thereof. Examples of a carbohydrate that can be used as a biocompatible matrix include agarose, agar, alginate, starch and its derivatives, dextrans, cellulose and its derivatives (e.g., methyl cellulose), glycodendrimers, or combinations thereof. Examples of an inorganic materials that can be used as a biocompatible matrix include hydroxyapatite, tricalcium phosphate, silicates and/or from glass, ceramics, carbon, fullerenes. In addition, any derivatives of such materials and/or composite materials of such materials and/or mixtures thereof can be used as a biocompatible matrix.

In a particular aspect, the biocompatible matrix is biodegradable.

As will be appreciated by those of skill in the art, the biocompatible matrices can be dissolved in appropriate diluents and used as coating for nondegradable or degradable biomaterials, or in admixture and thus constituent of degradable biomaterials, respectively. The biomaterials in question can be water soluble, soluble in organic solvents, and include but are not limited to polyglycolic acid, polygalactic acid, caprolactonic acid, acrylates, gelatin, collagen, hyaluronic acid and derivatives, fibrin and modifications, keratin, chitin, chitosan, silicone and silicates, titanium, steel, steel alloys, precious metals, copper, ceramics, glass, fibroins (both spider and silkworm), elastin, cellulose, methyl cellulose, starch, polystyrene, polybutyrate phthalate, agarose, agar, alginate. The application mode involves blending of predissolved HIF inducers and lysophospholipids to solutions of biomaterials which then harden, polymerise, or gel forming threads, meshworks, foams or solid blocks. Thus a biomateral is created that, upon dissolving, releases the compound.

The biocompatible matrices can be created by electrospinning, extrusion, printing, fusion deposition, gelation including thermal gelation, salt leaching, sintering, recombinant expression, layer by layer deposition, smelting, alloying, freeze-drying, spraying, chemical crosslinking, biological crosslinking, photo and UV crosslinking, and/or dehydrothermal crosslinking. The biocompatible matrices can be used as films, 2D or 3D sponges, meshworks, nanofibers, microfibers, nanorods, micropellets, capsules, foams, braided fibers, knitted fibers, mono and polyfilic threads, capsules, endoprostheses, hydrogels, and/or 2D or 3D coatings.

In the methods and compositions provided herein, the one or more agents that induce HIF-1α are used to stimulate one or more cell types that support and maintain functional blood vessels in an individual. In particular aspects, one or more agents that induce HIF-1α, and one or more agents that induce HIF-1α in combination with one or more lysophospholipids are used to induce angiogenesis in the presence of one or more cell types that support and maintain functional blood vessels. In one aspect, the cells that support and maintain functional blood vessels are endogenous cells of an individual. In other aspect, the compositions and methods described herein can further comprise one or more cell types (exogenous cell types) that support and maintain functional blood vessels. In particular aspects, the cells include one or more cell types that produce angiogenic factors, one or more cell types that induce angiogenesis or a combination thereof.

The exogenous cells can be obtained from the individual being treated, from other individuals or from commercial sources. Thus, the exogenous cells can be autologous cells, allogeneic cells, syngeneic cells, xenogeneic cells, chimeric cells, synthetic cells and the like.

As will be appreciated by those of skill in the art, a variety of cell types can be used. In particular aspects, the cells include endothelial cells, endothelial progenitor cells or lineages thereof, or combinations thereof; and/or mesenchymal cells, mesenchymal progenitor cells (e.g., mesenchymal stem cells and mesenchymal strom cells from, e.g., bone marrow, the perivascular niche of a tissue, placenta, umbilical cord, adipose tissue derived stem cells, stem cells derived from amniotic fluid, urine, breast milk or combinations thereof) or lineages thereof, hematopoietic cells, hematopoietic progenitor cells or lineages thereof, or combinations thereof.

Examples of cells from the lineages comprise fibroblasts, myofibroblasts, osteoblasts, chondrocytes, smooth muscle cells, skeletal muscle cells, heart muscle cells, monocytes, macrophages, lymphocytes, granulocytes, megakaryocytes, dendritic cells, astrocytes, mast cells, cardiomyocytes, pericytes or a combination thereof.

Other additional cells include stem cells, neuroectodermal and endodermal origin including epithelial cells of outer and inner surfaces of the human body such as keratinocytes, urothel, melanocytes, neuronal cells, neuroglia, hepatocytes, endocrine pancreas epithelium.

As will be appreciated by those of skill in the art, the methods and compositions provided herein can be used in a variety of sites of an individual in need thereof. Examples of sites include a wound (e.g., amputation; chronic wound such as a venous wound, diabetic wound, ulcer), a graft (cell, tissue, organ, bone, skin), a prosthetic device, a suture, an area of malperfusion (e.g., low perfusion such as in critical limb ischemia), an infarcted area (e.g., myocardial infarction, a stroke area (e.g., brain)), a bone fracture, an area of non-union in bone (e.g., a gap in bone that needs to be filled with, for example, cartilage or bone), an area at or near an implant or sensor (e.g., to facilitate perfusion around a sensor, such as a glucose sensor).

As described herein, the invention is directed to therapies aimed at conditions and/or diseases which require angiogenesis (therapeutic angiogenesis) in an individual in need thereof (e.g., therapies involving revascularization of a tissue/organ (e.g., infarcted hearts)). In one aspect, the therapy ameliorates the symptoms associated with the condition and/or disease in an individual.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact condition to be treated, the severity of the condition from which the patient suffers, the chosen route of administration, other drugs and treatments which the patient may concomitantly require, and other factors in the physician's judgment.

As used herein, an "effective amount" or "therapeutically effective amount" means an amount of the active compound that will elicit the desired biological or medical response in a tissue, system, subject, or human, which includes alleviation of the symptoms, in whole or in part, of the condition being treated.

The compositions (e.g., one or more agents that induce hypoxia, one or more lysophospholipids and combinations/matrices thereof) can be administered in a single dose (e.g., in a day) or in multiple doses. For example, the one or more agents that induce hypoxia and the one or more lysophospholipids can be administered together (at the same time) as a single composition or as separate compositions but at the same time. Alternatively, the one or more agents that induce hypoxia and the one or more lysophospholipids can be administered sequentially (administer one composition immediately after the other; administer one composition and after a time period administer the other composition). In addition, the one or more compositions can be administered in one or more days (e.g. over several consecutive days or non-consecutive days, weeks, months, years).

In the methods of the invention, the (one or more) site in the individual can be contacted with the compositions (e.g., one or more agents that induce hypoxia, one or more lysophospholipids and combinations/matrices thereof) described herein in a variety of ways. For example, the compositions can be administered systemically or locally to the individual. In one embodiment, the compositions are administered locally to the one or more sites (e.g., placed in direct contact with the one or more tissues, organs, prosthetics, blood vessels and the like). As will be appreciated by those of skill in the art, in one aspect, the site can be contacted with the compositions using a variety of methods. For example, the compositions could be transplanted alone or incorporated within, or as part of, a support (e.g., a scaffold; a gel) into e.g., a targeted tissue/organ (e.g., heart).

Another aspect, of the invention is a method of generating prevascularized tissue ex vivo. "Prevascularized tissue" refers to a blood vessel (vascular) network within a tissue before it is implanted into the body. The method comprises culturing (i) one or more agents that induce hypoxia induced factor 1α (HIF-1α), (ii) one or more cell types that produce angiogenic factors and (iii) one or more cell types that induce angiogenesis, thereby producing a culture. The culture is maintained under conditions in which angiogenesis occurs and prevascularized tissue forms, thereby generating prevascularized tissue ex vivo.

As will be appreciated by those of skill in the art, cell types that produce angiogenic factors include mesenchymal cells, mesenchymal progenitor cells or lineages thereof, hematopoietic cells, hematopoietic progenitor cells or lineages thereof, or combinations thereof, and cell types that induce angiogenesis comprise endothelial cells, endothelial progenitor cells or lineages thereof, or combinations thereof.

In a particular aspect, the method of generating prevascularized tissue ex vivo can further comprises including one or more lysophospholipids in the culture. In yet another aspect, the method of generating prevascularized tissue ex vivo can further comprises including a biocompatible matrix in the culture, whereby the prevascularized tissue forms on or within the biocompatible matrix.

In another aspect, the invention is directed to compositions produced by the method of generating prevascularized tissue ex vivo. In one aspect, the invention is directed to prevascularized tissue produced by the methods described herein. In another aspect, the invention is directed to a pharmaceutical composition comprising the prevascularized tissue.

Other compositions encompassed by the invention include a composition comprising (i) a biocompatible matrix, (ii) one or more agents that induce hypoxia induced factor 1α (HIF-1α) and (iii) one or more lysophospholipids. In a particular aspect, the biocompatible matrix is coupled to (e.g., coated; covalently coupled) the one or more agents that induce hypoxia induced factor 1α (HIF-1α) and the one or more lysophospholipids, for example, as a coated prosthesis (e.g., a coated hip prosthesis, a coated knee prosthesis); a sponge (e.g., collagen sponge) covalently coupled to, or soaked with, one or more agents that induce hypoxia induced factor 1α (HIF-1α) and one or more lysophospholipids. The composition can further comprise (iv) one or more cell types that produce angiogenic factors and (v) one or more cell types that induce angiogenesis.

In other aspects, the invention is directed to a pharmaceutical composition comprising (i) a biocompatible matrix, (ii) one or more agents that induce hypoxia induced factor 1α (HIF-1α) and (iii) one or more lysophospholipids. In yet other aspects, the pharmaceutical composition further comprises (iv) one or more cell types that produce angiogenic factors and (v) one or more cell types that induce angiogenesis.

The invention is also directed to a method of generating a vascular network in a device comprising culturing (i) one or more agents that induce hypoxia induced factor 1α (HIF-1α), (ii) one or more cell types that produce angiogenic factors and (iii) one or more cell types that induce angiogenesis, thereby producing a culture. The culture is maintained under conditions in which a vascular network forms in the device, thereby generating a vascular network in the device.

In particular aspects of the method the one or more cells types that induce angiogenesis are endothelial cells. Specific examples of such endothelial cells include human umbilical venous endothelial cells (HUVEC), microvascular endothelial cells (e.g., from dermis, placenta, adipose tissue, muscle, retina, brain and other neural tissue), arterial macrovascular endothelial cells (e.g., from arteries and aorta), lymphatic endothelial cells, outgrowth endothelial cells (e.g., from human peripheral blood buffy coat, outgrowth endothelial cells (e.g., from human bone marrow aspirate), endothelial cells generated from human embryonic stem cells, endothelial cells generated from induced pluripotent stem cells (iPSC), endothelial cells generated from mesenchymal stem cells (MSCs), endothelial cells generated from adult stem cells (ASCs) or combinations thereof.

In other aspects of the method, the one or more cells that produce angiogenic factors comprise fibroblasts. Examples of such fibroblasts include human lung fibroblasts (IMR-90), cancer fibroblasts from cancer stroma, primary fibroblasts from any fibroblast containing tissue such as dermis, muscle, placenta and the like.

In a particular aspect, the one or more cell types that induce angiogenesis and/or produce angiogenic factors are present in a medium (e.g., gel; hydrogel) that, for example, provides control over solutes concentration gradients and/or allows visualization of angiogenic events such as sprouting and length/direction of sprouts. In a particular aspect, the one or more cells that produce angiogenic factors are encapsulated, for example, in alginate beads.

In other aspects, the device used in the method of generating a vascular network can further comprise one or more lysophospholipids.

In yet other aspects, the device used in the method of generating a vascular network can further comprise a biocompatible matrix.

In still other aspects, the device used in the method of generating a vascular network can further comprise a control (e.g., an area of the device in which prevascularized tissue will not form). As will be appreciated by those of skill in the art, a variety of controls can used and will depend upon the use for which the prevascularized network is being used. In a particular aspect, the control comprises encapsulated alginate beads that do not contain cells.

As will also be appreciated by those of skill in the art, a variety of devices can be used in the methods of generating a prevascular network. In a particular embodiment, the device is a microfluidic device.

The invention is also directed to a vascular network produced by the methods provided herein.

In yet another aspect, the invention is directed to an angiogenic assay device comprising (i) one or more agents that induce hypoxia induced factor 1α (HIF-1α), (ii) one or more cell types that produce angiogenic factors and (iii) one or more cell types that induce angiogenesis, wherein the one or more cell types that induce angiogenesis form a vascular network in the presence of the one or more agents that induce HIF-1α and the one or more cell types that produce angiogenic factors in the device.

In a particular aspect, the device further comprises one or more lysophospholipids.

In yet another aspect, the device further comprises a biocompatible matrix.

As described herein, the one or more compounds described, used or generated in the methods described herein can be administered to a subject as part of a pharmaceutical composition. Formulations will vary according to the route of administration selected (e.g., solution, emulsion or capsule). A "pharmaceutical composition" comprises a (one or more) chemical compound described herein as the active ingredient and inert ingredient(s), such as pharmaceutically acceptable excipients, that make up the carrier. Standard pharmaceutical formulation techniques can be employed, such as those described in Remington™ Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hanks™ solution, Ringer™ lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Any suitable route of administration can be used, for example, local (e.g., administration/implantation at the site in need of angiogenesis), oral, dietary, topical, transdermal, rectal, parenteral (e.g., intravenous, intraarterial, intramuscular, subcutaneous injection, intradermal injection), inhalation (e.g., intrabronchial, intranasal or oral inhalation, intranasal drops), ocular, pulmonary, nasal, and the like may be employed. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like.

The data provided herein show that agents that induce HIF (e.g., PHi) works synergistically with lysophospholipids (e.g., S1P) in promoting angiogenesis in the in vitro microfluidic model. Thus, the combination of agents that induce HIF-1α and lysophospholipids can be utilized in tissues either for the application of tissue engineering or for therapeutic angiogenesis.

Thus, provided herein are compositions and methods that induce angiogenesis by combining angiogenic and antifibrotic effects and priming tissue with lysophospholipids that induce longer viability of endothelium. The compositions and methods can induce vascularization (e.g., neovascularisation) of a site in an individual, e.g., by inducing and luring sprouting capillaries from around the implanted compositions into the implanted compositions. In particular embodiments, fibrotic capsule formation is prevented from forming around the implant. In addition, the compositions and methods can be used to prevascularise in vitro tissue constructs before implantation, and thus, can be used as a type of wound dressing that can be used, for example, in chronic non-healing wounds to induce vascularisation.

The compositions and methods can be used for a variety of purposes, such as for ex vivo prevascularizing grafts in an endothelial coculture setting (static or in bioreactor) by immersion or perfusion with such substances; locally releasing angiogenic inducing agents to locally induce angiogenesis/neovascularisation of implants with or without cells upon implantation; locally inducing HIF and improving vascular integrity by releasing the angiogenic inducing agents in the immediate vicinity of an implant; locally delivering angiogenic agents from wound care materials (e.g., dressings; bandages and the like).

Specific examples of the use of the compositions and methods include fibrin gel matrices which can be prepared by mixing the following components at the final concentrations of 10 mg/mL fibrinogen (Fluka AG), 2 U/mL factor XIII (Baxter AG, Vienna), and 2.5 mmol/L CaCl2. HIF inducers can be mixed with lysophospholipids and then added to the fibrinogen solution before initiation of fibrin gelation by addition of thrombin. The preferred concentration range depends on the potency of the respective HIF inducer and lysophospholipid and the velocity of the degradation. Preferred concentrations are 5-30, in particular 10 µg/ml CPX, 10 mM PDCA, 100-500 µM hydralazine (for example) and 250 nM S1P.

The skilled artisan will recognize that the judicious choice of reactants, solvents, and temperatures are important considerations in any successful coupling. Determination of optimal conditions, etc., is routine. Thus, the skilled artisan can make a variety of compounds using the guidance of the scheme above and other schemes applying to other materials.

The biomaterials comprising HIF-inducers and lysophospholipids can be seeded with a mixture of cells belonging to two different groups. Group 1 comprises endothelial progenitor cells or preferably endothelial cells. Group 2 are derived from mesenchymal and haematopoetic progenitors including but not being restricted to lineages like fibroblasts, myofibroblasts, osteoblasts, chondrocytes, smooth muscle cells, skeletal muscle cells, heart muscle cells, monocytes, macrophages, astrocytes, mast cells, cardiomyocytes and pericytes. These cocultures are seeded as a mixture or sequentially. In the latter case Group 2 cells are seeded first, and Group 1 cells later or vice versa, depends on the designs and properties of biomaterials. The seeding into a given scaffold can be augmented using hydrogels, collagen gels, fibrin glue and similar formulations. The seeded scaffolds are kept in static culture or in bioreactors under flow conditions. The released HIF-inducers from the scaffold material then stimulate Group 2 cells to produce angiogenic factors which in turn will induce angiogenesis in Group 1 cells. Concurrently, lysophospholipids could further enhance the secretion of angiogenic factors by Group 2 cells or help activate Group I cells thus making them more responsive to the angiogenic factors being secreted by Group 2 cells. This will create a prevascularised tissue that can implanted into desired locations where the precreated capillary bed will be targeted by surrounding capillary stumps and integrated into the general perfusion of the tissue region by fusion of the host and graft capillary system (inoculation) thus ensuring survival of the implanted graft (inside out approach).

In another aspect, cell free biomaterials, are implanted into desired body locations, whereby the implanted biomaterial released HIF inducing substances and lysophospholipids locally and thus activates surrounding tissue to send capillary sprouts into the biomaterial (outside in approach).

In yet another aspect, degradable biomaterials containing HIF-inducing substances and lysophospholipids are used as suturing material.

Biodegradable poly(lactide-co-glycolide) (PLGA) fibers are promising drug carriers. Drugs can be incorporated into fibers and released as PLGA is hydrolyzed. The drug release rate is partially dependent on the rate of hydrolysis of the PLGA fibers, threads or meshes which is affected by molecular weight, copolymer composition and fiber morphology. These fibers are used as polyfilic or monofilic threads for the suturing of tissue. While the sutures are degraded by the surrounding tissue, the local release of HIF-inducers and lysophospholipids will increase the local angiogenesis and reduces local scarring. The preferred embodiment will be 10% L-lactide/90% glycolide (polyglactin 910).

Another aspect involves coating of predissolved HIF inducers and lysophospholipids to a biomaterial, thus the surface delivers the HIF inducing substances and lysophospholipids within a certain time window.

In yet another aspect, PLGA scaffolds are soaked in HIF-inducing substance and lysophospholipids containing solutions. After incubation and swelling preferably overnight scaffolds are subjected to freeze drying. Alternatively HIF-inducing substances and lysophospholipids are admixed to a biomaterial in the fluid phase which then is used to coat a given scaffold. Preferably thermal gelation of PEG/PLGA tri block copolymers would be a mode of action here. In another application surfaces of prostheses are activated using air, argon or any other plasma and are immediately after treatment coated with HIF inducing substances and lysophospholipids-containing solutions.

The skilled artisan will recognize that the judicious choice of reactants, solvents, and temperatures and pressure is an important consideration in any successful coating procedure. Determination of optimal conditions, etc., is routine. Thus, the skilled artisan can make a variety of compounds using the guidance of the scheme above.

In another aspect, predissolved HIF inducers can be coupled to the surface of a biomaterial, involving spacers that are cleavable by radicals or proteolytic enzymes. This allows specific release on cellular demand.

In yet another aspect, HIF inducing substances and lysophospholipids are thiolated as known to those skilled in the art of chemical synthesis and coupled to a peptide combining a plasmin cleavage site and the factor XIIIa substrate sequence CKTYKNQEQVSPL via usual coupling reactions. The coupled HIF inducer and lysophospholipids are then added to the preparation of fibrin gel matrices which are prepared by mixing the following components at the final concentrations of 10 mg/mL fibrinogen (Fluka AG), 2 U/mL factor XIII within the fibrinogen solution before initiation of fibrin gelation by addition of thrombin. The Factor XIIa sequence is attached covalently via epsilon lysyl gamma glutamyl isodipeptide crosslinks to the fibrin scaffold. Cells invading the scaffold and expressing plasmin on their surface or secreting it will liberate the HIF-inducer and thus activate themselves or bystanding cells.

The skilled artisan will recognize the judicious choice of reactants, solvents, and temperatures are important considerations in any successful coupling. Determination of optimal conditions, etc., is routine. Thus, the skilled artisan can make a variety of compounds using the guidance of the scheme above.

In another aspect, small particles of degradable biomaterial containing said substances can be created. These particles are delivered via biolistic delivery employing a short pressure pulse.

The Helios gene gun (BioRad) is a convenient, hand-held device that was originally designed to provide rapid and direct gene transfer into a range of targets in vivo. The unit uses an adjustable low-pressure helium pulse to sweep DNA- or RNA-coated gold microcarriers from the inner wall of a small plastic cartridge directly into the target. Instead of different nucleic acids the HIF inducers and lysophospholipids are either deposited onto gold particles or microparticles made of f.e. fibrin, PCL, or PLGA with diameter ranging from 0.5 um to 2 μm are used to deliver HIF inducers and lysophospholipids. Dry Micropellets containing HIF inducers and lysophospholipids are loaded into a helium driven gun (f.e. Helios Gene gun by Bio-Rad) and are injected into tissue. This can be done through intact surfaces of skin or mucosa or into tissue constructs ex vivo on into surgical sites in vivo.

In other aspects, the HIF inducing substances are blended into the biomaterial and/or are part of a degradable coating of the biomaterial and/or are affixed to the biomaterials by bonds that are cleavable by proteolytic enzymes or radicals. In addition, the lysophospholipids are also blended into the biomaterial and/or are part of a degradable coating of the biomaterial and/or are affixed to the biomaterials by bonds that are cleavable by proteolytic enzymes or radicals. The cleavable bonds represent spacers containing cleavage motifs for proteolytic enzymes preferentially but not limited to trypsin, chymotrypsin, chymase, cathepsin, plasmin, uroplasmin, matrix metalloproteinases (MMP's), thrombin, C1-esterase, serineproteases, cysteine proteases.

The invention solves the problem of local angiogenesis induction and antifibrosis, using stable pharmacological compounds that are not dependent on liver activation. The substances are delivered to the point of need, i.e. abolishing the need to administer systemically with expectable side effects and without the dependency on stable incorporation of cDNA.

Advantages over existing methods are the combinatorial effects of both antifibrosis and angiogenesis, the abolished necessity to do DNA/gene transfer into cells before, during or after transplantation and the local delivery. The invention abolishes the need to synthesise peptide factors that either only tackle a portion of the angiogenic pathways (like VEGF) or afford larger synthetic efforts (like oxygen-insensitive HIF-1α peptide. Important advantages are that some of HIF-inducing substances, namely hydralazine and ciclopirox olamine are already FDA-approved drugs.

The compositions and methods can be used to connect implantable sensors (e.g., that measure blood chemicals (fe. glucose)) into the blood system. In addition, the inventions provided methods and compositions that allow implants/scaffolds that are not seeded with cells can get rapidly vascularised (f.e. bone, nerve conduits, cardiac patches; implants that are seeded with cells, can get rapidly vascularised (e.g., pancreatic islet cells, encapsulated hepatocytes, cardiomyocyte patches etc); encapsulated tissues and cells in permselective materials to close connection to the circulation (e.g., pancreatic islet cells); prevascularisation of tissue constructs in static and bioreactor culture conditions (e.g., muscle, bone, soft tissue as such etc) using endothelial cells or progenitor cells; for an administrative route of HIF inducing drugs and lysophospholipids via local drug delivery which includes osmotic pumps, biolistic particles releasing drugs (micro and nanoscale), scaffolds that partially degrade and release the drugs, or coatings of scaffolds that set the drugs free, in particular meshed scaffolds, nano and microfibers, scaffold made by fusion deposition, extrusion, salt leaching, layer by layer construction, foaming, gelling; advanced wound care materials that are used as bandage or to cover chronic wounds, e.g., materials locally releasing the drug which can be made e.g., from alginates, hydrogels; suturing material that releases the drugs and lysophospholipids while being degraded, thereby accelerating wound healing; encapsulating material for stem cells (adult, embryonic) autologous or allogeneic for protection and/or immunoisolation; biolistic application of micro- or nanoparticles releasing said drugs can be advantageous in inducing local microcirculation on a sustained release basis for surgical free flaps; small implants into wound areas in dental oral surgery to accelerate vascularisation e.g., of periodontium; breast implants that do not lead to a capsule formation and attended complications; pads for covering chronic non-healing wounds that contain and release HIF inducers and lysophospholipids to locally accelerate wound healing and tissue regeneration; coating of silicone implants for breast augmentation with the aim to locally deliver the HIF inducers and lysophospholipids which leads to a better vascularised tissue and a significantly reduced fibrous capsule; fabrication of sensors, e.g., glucose sensors, mostly of biomaterials that locally release HIF-inducing substances and lysophospholipids which leads to sensors that upon implantation will get better access to the perfusion of the surrounding tissue and thus will lead to better and more accurate online realtime measurements, e.g., of blood glucose level.

EXEMPLIFICATION

Example 1

Induction of Angiogenesis in Microfluidic Devices Using Prolyl Hydroxylase Inhibitors and Sphingosine-1 Phosphate Angiogenesis represents a major challenge in regenerative medicine and tissue engineering. The synergistic effects of PHis and S1P were studied in an in vitro microfluidic platform where endothelial cells were co-cultured with fibroblast cells and subjected to the stimulation of PHis and S1P. Shown herein is that the interactions between endothelial cells and mesenchymal cells or fibroblasts maintain immature sprouts and turn them into functional vessels with lumens and these effects are most prominent with PHis and S1P. Thus, PHis worked synergistically with S1P.

The pro-angiogenic effects of PHis and S1P were studied on human umbilical venous endothelial cells (HUVEC) whereby fibroblasts in a neighbouring channel served as angiogenic secretory cells when stimulated by PHis and S1P. As shown herein, synergistic effects of PHis and S1P developed functional vascular network in microfluidic platform.

Microfluidic devices with the capability of accommodating IMR-90 (human lung fibroblasts) encapsulated alginate beads were used as they offered excellent control over solutes concentration gradient and allowed observation of sprouting events in 3D collagen regions. The microfluidic devices were made using standard soft lithography methods and alginate beads were generated as described earlier (Vickerman et al., 2008, Kim et al., 2009).

HUVECs were seeded in the middle channel. Alginate beads were introduced into left and right channels after HUVECs formed a monolayer.

HUVECs formed a monolayer on collagen gel as well as top and bottom of the channel. Hoechst stained nuclei (blue), rhodamine phalloidin stained actin (red) and Alexa fluor 488 immunostained VE-cadherin (green). Scale bar denotes 50 µm Results IMR-90 Cells Help Maturation of Sprouts Ciclopirox olamine (CPX), a type of PHi was used in combination with S1P in all three channels in microfluidic devices. Immature sprouts that were observed on day two turned into vessels, if they were growing towards IMR-90 encapsulated beads, on day four. On the other hand, the immature sprouts broke off from the monolayer and migrated randomly in collagen on the side that was towards empty alginate beads. Hence, the importance of mesenchymal-endothelial cells interactions was shown in the microfluidic model.

Vascular Network-Like Structure with Lumen

In conventional 2D angiogenesis model, capillary-like structure (CLS) is commonly used as assessment for degree of angiogenesis.

Conclusion

Shown herein were the synergistic effects of CPX and S1P in a 3D endothelial-mesenchymal co-culture model.

Example 2

CPX Induces Secretion of Complementary Angiogenic Proteins from Both Fibroblasts and Endothelial Cells As the experimental set-up favoured soluble factors as messengers between the two cell types the secretion of angiogenic factors by fibroblasts and endothelial cells in the presence of CPX and S1P, respectively, was assessed.

Proteome profiler data indicated the increased secretion of several proteins including PlGF (6 fold), IL-8 (3 fold), EGF (2.9 fold) and endothelin-1 (1.5 fold) by CPX+S1P by endothelial cells. Highly comparable increases were found in the presence of CPX alone, and none were observed with S1P only.

Figure 1:
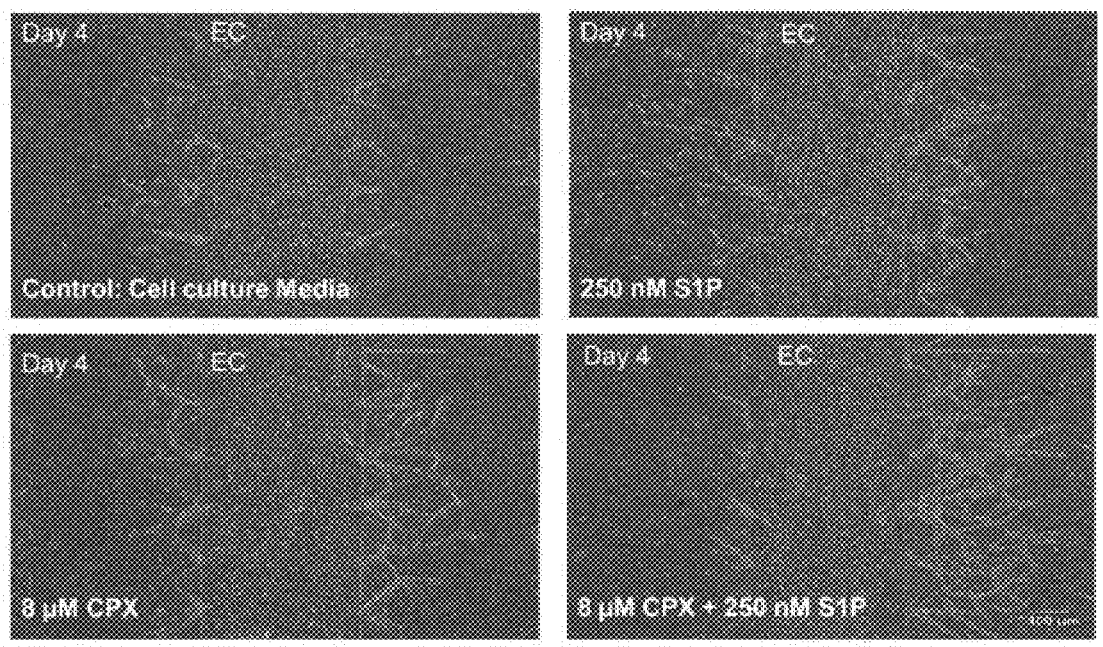
FIG. 1: 4× Phase contrast images of devices treated with just cell culture media (control), just S1P, just CPX and the combination of both CPX and S1P. Sprouts on right side were growing towards IMR-90 encapsulated beads while left side were towards empty alginate beads. Ciclopirox olamine (CPX), a type of PHi was used in combination with S1P in all three channels in microfluidic devices. Immature sprouts that were observed on day two would turn into vessels, if they were growing towards IMR-90 encapsulated beads, on day four. On the other hand, the immature sprouts would break off from the monolayer and migrate randomly in collagen on the side that was towards empty alginate beads. Hence, the importance of mesenchymal-endothelial cells interactions was once again being confirmed in our microfluidic model. Red lines denote the approximated length of sprouts which show that CPX worked synergistically with S1P in promoting angiogenesis as compared to the other three conditions. The scale bar denotes 100 μ.m.
Figure 2:
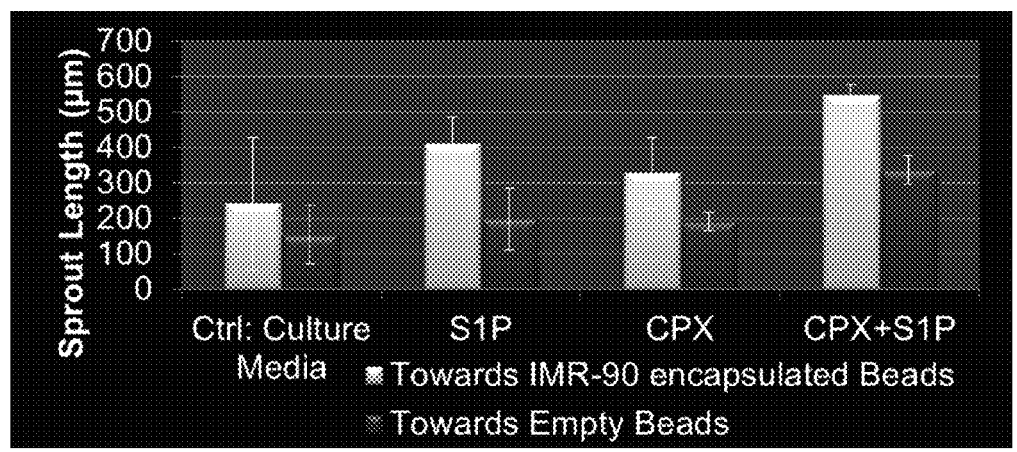
FIG. 2: Length of sprouts towards IMR-90 encapsulated beads and towards empty beads. Sprout length is consistently higher on cells encapsulated beads side in all conditions. This result shows that CPX and S1P act synergistically in forming longer sprouts as compared to sole induction by either S1P or CPX.
Figure 3:
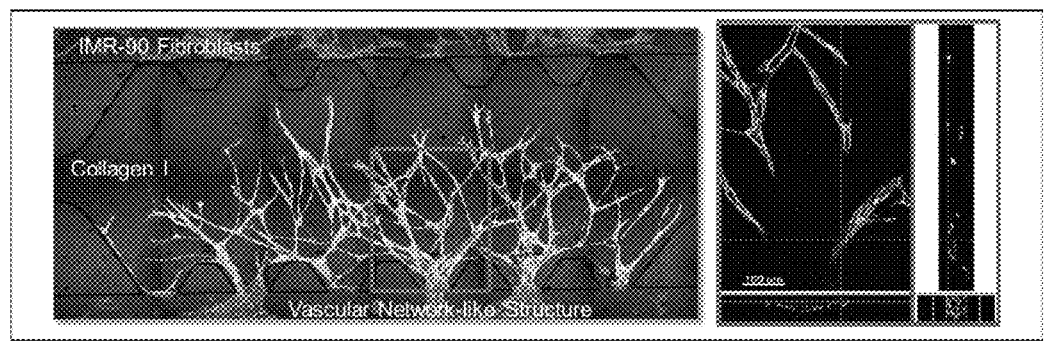
FIG. 3: 20× confocal images of Hoechst stained nuclei (blue), rhodamine phalloidin stained actin (red) and Alexa fluor 488 immunostained VE-cadherin (green) showed sprouts anastomose under 8 μM CPX and 250 nM S1P induction and section image of it proved that the sprouts were with lumina. Scale bar denotes 100 μm.
Figure 4:
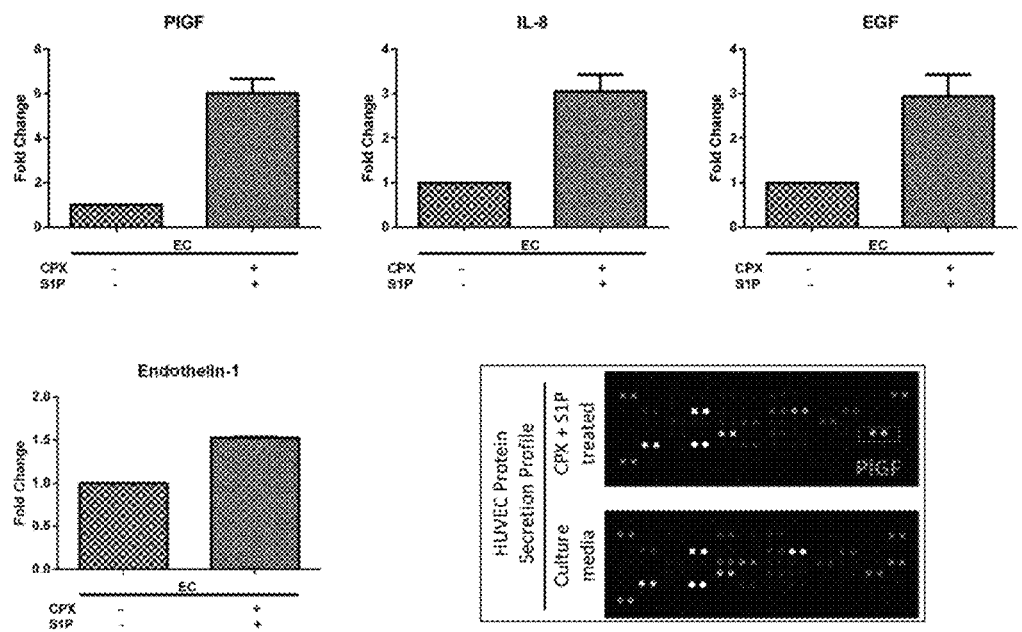
FIG. 4: CPX and S1P induce secretion of different angiogenic proteins by endothelial cells and fibroblasts. (A-D): proteomic analysis plots of proteins upregulated in HUVEC treated with CPX+S1P. The upregulated proteins are PlGF (6.0×), IL-8 (3.0×), EGF (2.9×) and endothelin-1 (1.5×). (F-I): proteomic analysis plots of proteins upregulated in IMR-90 fibroblasts treated with CPX+S1P. The upregulated proteins include HGF (1.4×), IGFBP-2 (1.6×), uPA (1.8×)
Figure 4:
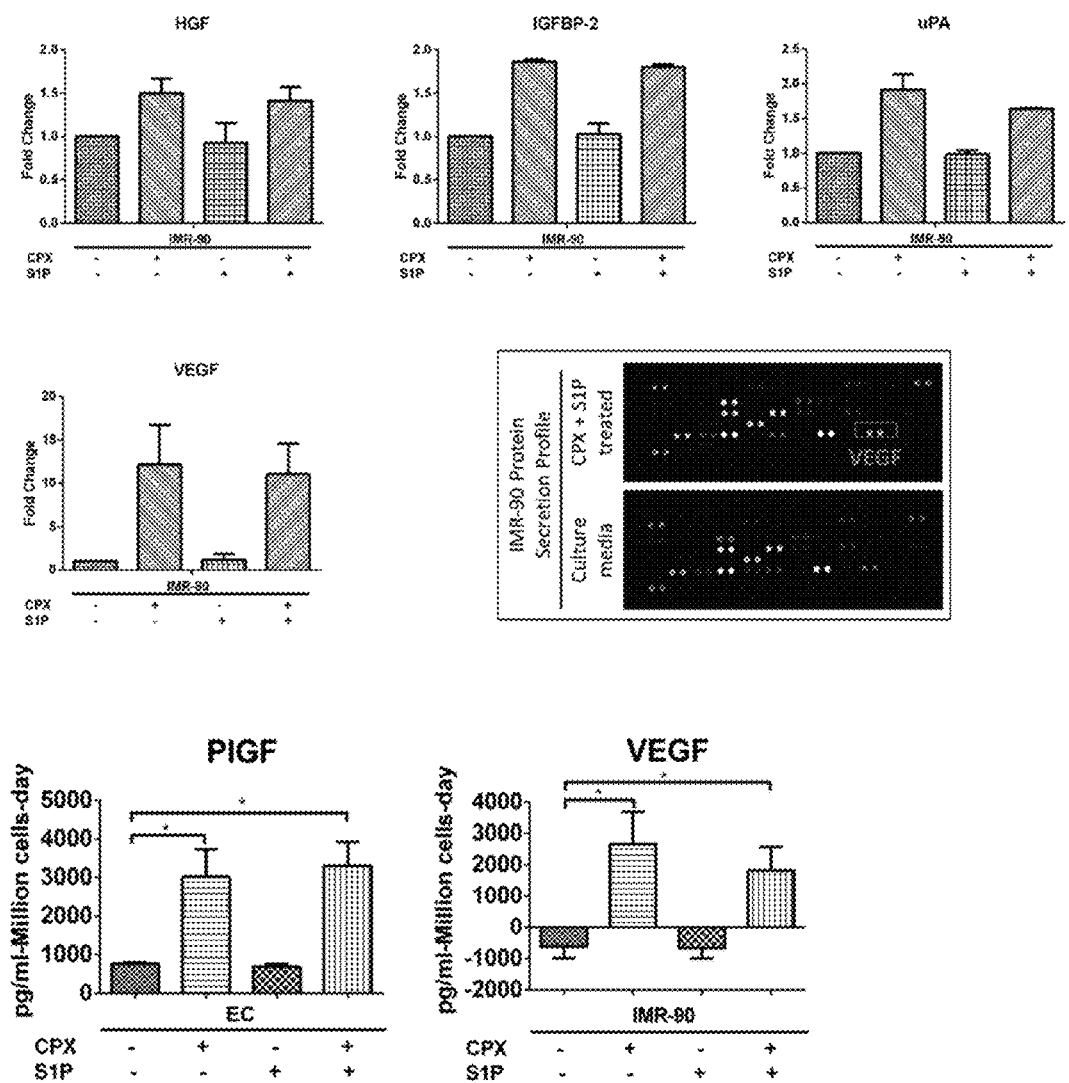

In fibroblasts, CPX+S1P expression of HGF (1.4 fold), IGFBP-2 (1.8 fold), uPA (1.6 fold) and VEGF (11 fold). Highly comparable increases were found in the presence of CPX alone, and none were observed with S1P only. These data were validated for PlGF and VEGF through ELISA. It was found that CPX+S1P can increase the PlGF secretion rate in endothelia from 765.5±37.1 (±standard error) pg/ml-Million cell-day to 3297±631.8 (±standard error) pg/ml-Million cell-day while S1P did not show any effect. In fibroblasts an increase of VEGF secretion which was 1819±754.1 (±standard error) pg/ml-Million cell-day was confirmed. Again, S1P alone did not elicit measurable effects. See FIG. 4.

TABLE 1

Angiogenic proteins secreted by EC and fibroblasts treated with CPX + S1P

| Proteins | Fibroblasts | HUVEC | Upregulated by |
|---|---|---|---|
| HGF | + (++) | − | CPX |
| IGFBP-2 | + (++) | − | CPX |
| uPA | + (++) | − | CPX |
| VEGF | + (++) | − | CPX |
| Endothelin-1 | − | + (++) | CPX |
| PlGF | − | + (++) | CPX |
| EGF | − | + (++) | |
| IL-8 | + | + (++) | |
| MCP-1 | + (+) | + (−−) | Endothelial CM |

"+" denotes protein secretion spontaneously;
"−" denotes no protein secretion spontaneously;
"(++)" denotes upregulation of protein secretion when treated with CPX + S1P;
"(−−)" denotes downregulation of protein secretion when treated with CPX + S1P;
"(+)" denotes upregulation of protein secretion by endothelial CM Example 3

Endothelial Cells CM Increases MCP-1 Secretion by IMR90

To study the influence of endothelial cells on fibroblasts IMR90 cells were cultured in EC conditioned medium with or without the addition of CPX+S1P, and quantified factors secreted by fibroblasts by ELISA. Fibroblasts showed a basal secretion of MCP-1. Endothelial cell CM induced the secretion of MCP-1 by fibroblasts by 3-fold in the absence of any CPX+S1P induction, however, the combination of both pharmacological agents increased MCP-1 secretion by a further 20%. As monosubstances, neither S1P nor CPX were able to increase basal MCP-1 secretion. See FIG. 5.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of inducing angiogenesis at a site in an individual in need thereof comprising administering locally to the site an effective amount of ciclopirox olamine (CPX) and sphingosine 1-phosphate (S1P).

2. The method of claim 1 wherein the CPX and S1P are present in a biocompatible matrix that is administered locally to the site.

3. The method of claim 1 wherein the CPX and S1P are administered with one or more cell types that support and maintain functional blood vessels.

4. The method of claim 1 wherein the site in the individual is a wound, a graft, a prosthetic device, a suture, an area of malperfusion, an infarcted area, a bone fracture, an area of non-union in bone, an area at or near an implant or sensor.

* * * * *